US012700092B2

(12) United States Patent
Naruse

(10) Patent No.: US 12,700,092 B2
(45) Date of Patent: Aug. 4, 2026

(54) IMAGE PROCESSING DEVICE, ENDOSCOPE SYSTEM, IMAGE PROCESSING METHOD, AND INFORMATION STORAGE MEDIUM

(71) Applicant: OLYMPUS CORPORATION, Tokyo (JP)

(72) Inventor: Masato Naruse, Kunitachi (JP)

(73) Assignee: OLYMPUS CORPORATION, Tokyo (JP)

( * ) Notice: Subject to any disclaimer, the term of this patent is extended or adjusted under 35 U.S.C. 154(b) by 328 days.

(21) Appl. No.: 18/522,938

(22) Filed: Nov. 29, 2023

(65) Prior Publication Data

US 2024/0095919 A1 Mar. 21, 2024

Related U.S. Application Data

(63) Continuation of application No. PCT/JP2021/022445, filed on Jun. 14, 2021.

(51) Int. Cl.
*G06K 9/00* (2022.01)
*A61B 5/02* (2006.01)
(Continued)

(52) U.S. Cl.
CPC ........ *G06T 7/0012* (2013.01); *A61B 5/02042* (2013.01); *G06T 7/70* (2017.01);
(Continued)

(58) Field of Classification Search
USPC ....... 382/100, 103, 128–133, 154, 156, 168, 382/173, 181, 254, 285–291, 305, 312;
(Continued)

(56) References Cited

U.S. PATENT DOCUMENTS

2015/0230875 A1 8/2015 Shademan et al.
2016/0038004 A1* 2/2016 Tanaka ................... A61B 90/37
600/371
(Continued)

FOREIGN PATENT DOCUMENTS

JP 2004-337257 A 12/2004
JP 2011-036371 A 2/2011
(Continued)

OTHER PUBLICATIONS

International Search Report dated Aug. 31, 2021 received in PCT/JP2021/022445.

*Primary Examiner* — Seyed H Azarian
(74) *Attorney, Agent, or Firm* — Scully, Scott, Murphy & Presser, P.C.

(57) ABSTRACT

An image processing device includes a processor. The processor is configured to: recognize blood vessel running information; recognize a first bleeding position from a surgery image; identify a second bleeding position in the blood vessel running information corresponding to the first bleeding position in the surgery image; and identify a bleeding stopping point corresponding to the second bleeding position as a bleeding stopping recommended point corresponding to the first bleeding position. The processor: acquires information about the bleeding stopping recommended point corresponding to each of one or more blood vessel areas in the blood vessel running information; identifies the blood vessel area among the one or more blood vessel areas, to which the second bleeding position belongs; and performs processing in which the bleeding stopping recommended point corresponding to the blood vessel area thus identified is superimposed on the surgery image and displayed on a display.

18 Claims, 15 Drawing Sheets

(51) Int. Cl.
    *G06T 7/00*          (2017.01)
    *G06T 7/70*          (2017.01)
    *G06V 20/50*        (2022.01)

(52) U.S. Cl.
    CPC .... *G06V 20/50* (2022.01); *G06T 2207/10068*
        (2013.01); *G06T 2207/20081* (2013.01); *G06T*
             *2207/30101* (2013.01); *G06V 2201/03*
                      (2022.01)

(58) Field of Classification Search
    USPC ........................................................ 600/371
    See application file for complete search history.

(56)                References Cited

U.S. PATENT DOCUMENTS

| | | | |
|---|---|---|---|
| 2019/0069769 A1 | 3/2019 | Kubo | |
| 2019/0159687 A1* | 5/2019 | Kubo | A61B 1/045 |
| 2019/0350448 A1* | 11/2019 | Kutsuma | H04N 1/62 |
| 2020/0297422 A1* | 9/2020 | Gocho | A61B 1/00055 |
| 2022/0020496 A1* | 1/2022 | Saito | G06T 7/0012 |
| 2022/0246307 A1* | 8/2022 | Nakamura | G16H 50/30 |

FOREIGN PATENT DOCUMENTS

| | | | |
|---|---|---|---|
| JP | 6342598 B1 | 6/2018 |
| WO | 2017/199509 A1 | 11/2017 |
| WO | 2019/116593 A1 | 6/2019 |

* cited by examiner

FIG.3

BLOOD VESSEL RUNNING
INFORMATION

RECOGNITION

ENDOSCOPIC IMAGE

MATCHING

CALCULATION OF
RECOMMENDED
POINT

BLEEDING STOPPING
RECOMMENDED POINT

BLEEDING STOPPING
RECOMMENDED
POINT

BLEEDING POINT
(FIRST BLEEDING POSITION)

BLEEDING POINT
(SECOND BLEEDING POSITION)

FIG.7

PRE-SIMULATION

EXTRACTION OF BLEEDING STOPPING
POINT CANDIDATE

BLOOD VESSEL RUNNING INFORMATION

ENDOSCOPIC IMAGE

IMAGE PROCESSING DEVICE, ENDOSCOPE SYSTEM, IMAGE PROCESSING METHOD, AND INFORMATION STORAGE MEDIUM

CROSS REFERENCE TO RELATED APPLICATIONS

This application is a continuation of International Patent Application No. PCT/JP2021/022445, having an international filing date of Jun. 14, 2021, which designated the United States, the entirety of which is incorporated herein by reference.

BACKGROUND OF THE INVENTION

Japanese Unexamined Patent Application Publication No. 2011-36371 discloses a medical image recording device which detects a bleeding area from image information during surgery. This medical image recording device displays a mark around the bleeding area on a display screen. In addition, this medical image recording device compares the amount of change of the bleeding area with a preset threshold, thereby determining condition of the bleeding area.

SUMMARY OF THE INVENTION

In accordance with one of some aspect, there is provided an image processing device comprising:

a processor, and a memory including a program, where the memory and the program are configured, with the processor, to cause the image processing device to:

acquire a surgery image captured by an endoscope;

recognize blood vessel running information indicating blood vessel running in a subject of the endoscope;

recognize a first bleeding position from the surgery image;

identify a second bleeding position in the blood vessel running information corresponding to the first bleeding position in the surgery image;

acquire information about a bleeding stopping recommended point corresponding to each of one or more blood vessel areas in the blood vessel running information;

identify the blood vessel area among the one or more blood vessel areas, to which the second bleeding position belongs; and perform processing in which the bleeding stopping recommended point corresponding to the identified blood vessel area is superimposed on the surgery image and displayed on a display.

In accordance with one of some aspect, there is provided an image processing method, comprising:

recognizing blood vessel running information indicating blood vessel running in a subject of an endoscope;

recognizing a first bleeding position from a surgery image captured by the endoscope;

identifying a second bleeding position in the blood vessel running information corresponding to the first bleeding position in the surgery image;

acquiring information about a bleeding stopping recommended point corresponding to each of one or more blood vessel areas in the blood vessel running information;

identifying the blood vessel area among the one or more blood vessel areas, to which the second bleeding position belongs; and performing processing in which the bleeding stopping recommended point corresponding to the identified blood vessel area is superimposed on the surgery image and displayed on a display.

In accordance with one of some aspect, there is provided a non-transitory information storage medium storing a program causing a computer to execute:

recognizing blood vessel running information indicating blood vessel running in a subject of an endoscope;

recognizing a first bleeding position from a surgery image captured by the endoscope;

identifying a second bleeding position in the blood vessel running information corresponding to the first bleeding position in the surgery image;

acquiring information about a bleeding stopping recommended point corresponding to each of one or more blood vessel areas in the blood vessel running information;

identifying the blood vessel area among the one or more blood vessel areas, to which the second bleeding position belongs; and performing processing in which the bleeding stopping recommended point corresponding to the identified blood vessel area is superimposed on the surgery image and displayed on a display.

BRIEF DESCRIPTION OF THE DRAWINGS

FIG. 3 is a second example configuration of the endoscope system.

FIG. 7 is an example configuration of a training device and an endoscope system.

DETAILED DESCRIPTION

Figure 1:
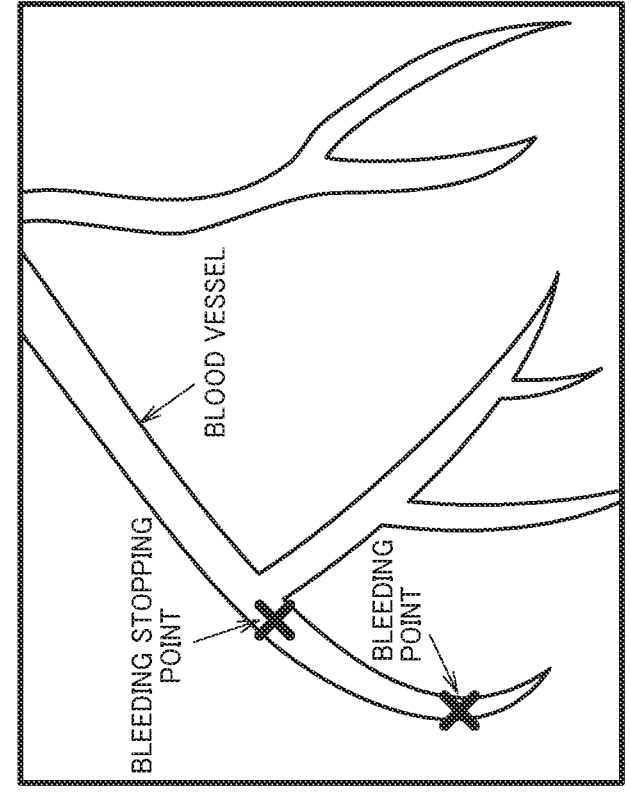
FIG. 1 is a diagram illustrating a bleeding stopping treatment during surgery using an endoscope.
Figure 1:
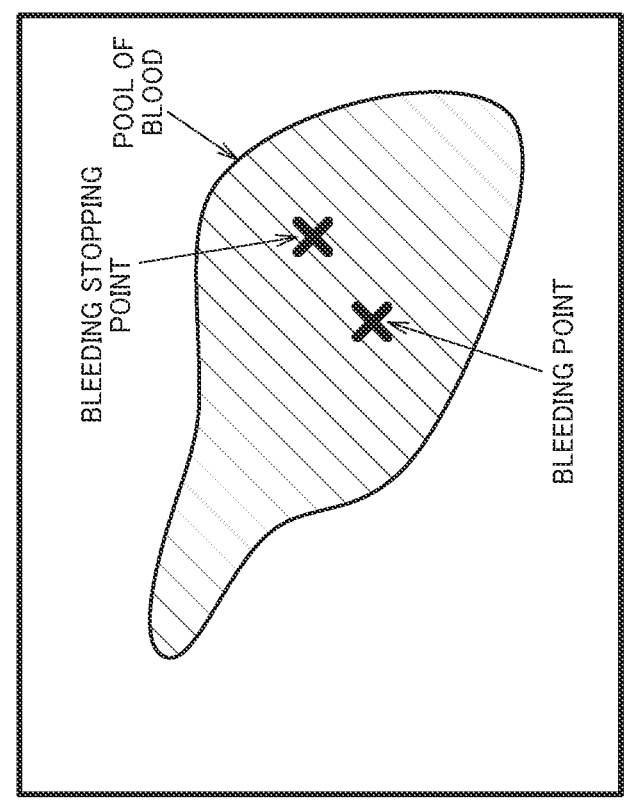

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

1. First and Second Example Configurations

First, a bleeding stopping treatment during surgery using an endoscope will be described. The bleeding stopping treatment includes a technique of cauterizing a bleeding point, a technique of stopping blood flow upstream of a bleeding point such as using a clip, etc. Assumed herein is the bleeding stopping treatment that stops blood flow upstream of a bleeding point using a clip and the like.

In the bleeding stopping treatment, it is required to decide a bleeding stopping point considering blood vessel running. When a surgeon cannot accurately recognize the blood vessel running upon stopping bleeding upstream of a bleeding point, the bleeding may not stop even if the bleeding stopping seems to be successful. For example, when an attached clip comes off which causes bleeding again, or new bleeding occurs for some reason, it may be desired to re-attach the clip to a blood vessel upstream of the bleeding point. However, as shown in the left figure of FIG. 1, there is a possibility that the bleeding stopping point cannot be recognized because a blood vessel cannot be seen in a surgery image due to a pool of blood. Or as shown in the right figure of FIG. 1, it is desired to stop bleeding of a blood vessel upstream of a bleeding position and downstream of a bifurcation, but it is impossible to accurately recognize bifurcation of a deep blood vessel. That is, depending on a depth from an organ surface, the blood vessel running may be difficult to recognize. Although the right figure of FIG. 1 only shows one example of the blood vessel running, blood vessels actually run at various depths from the surface of the organ.

Accordingly, in the bleeding stopping treatment, a system that can support identification of a bleeding stopping point by a surgeon is required. Specifically, in the bleeding stopping treatment, there is a need for a system that can present a bleeding stopping recommended point considering the blood vessel running.

Figure 2:
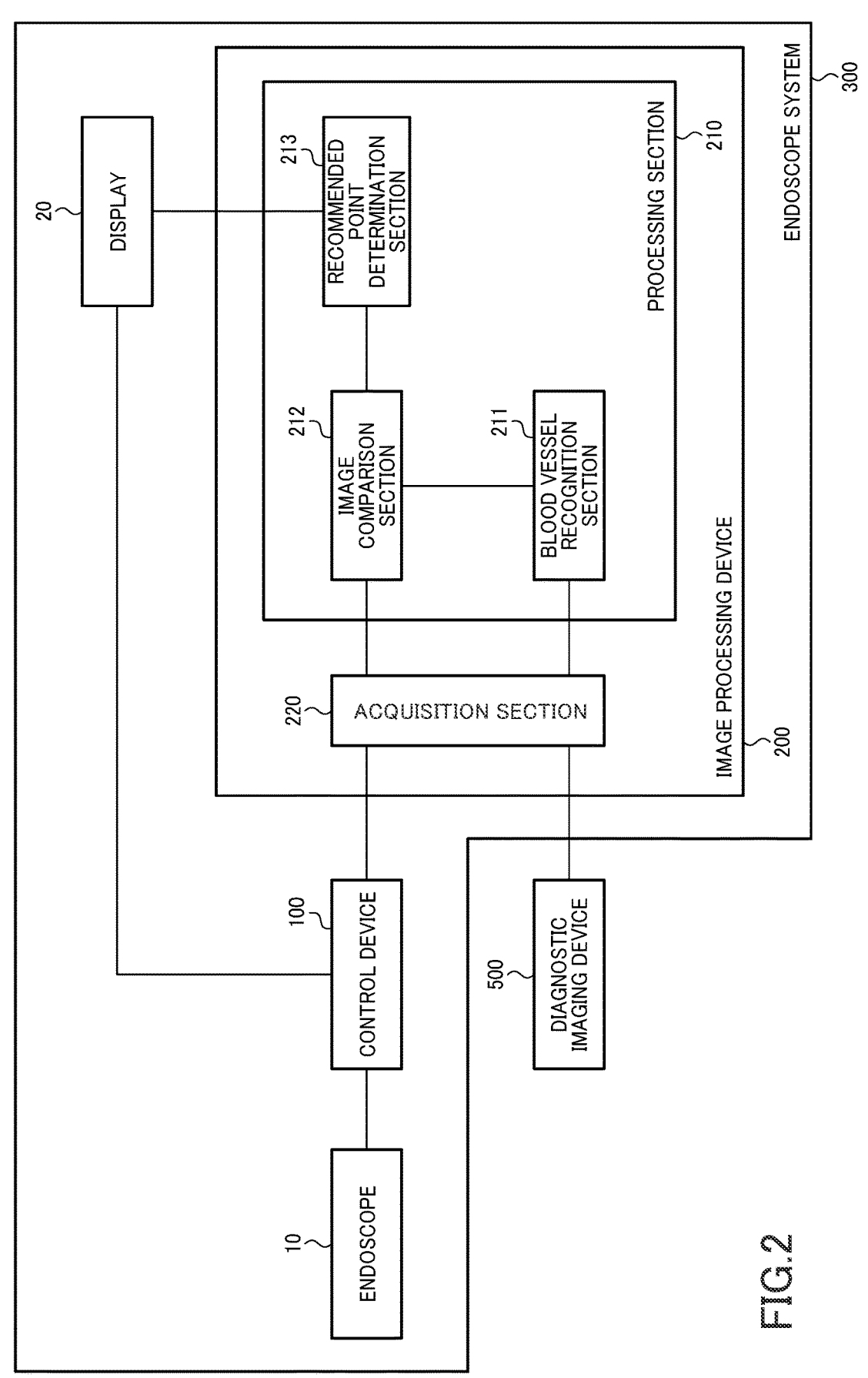
FIG. 2 is a first example configuration of an image processing device and an endoscope system.

FIG. 2 is a first example configuration of an image processing device 200 and an endoscope system 300 according to the present embodiment. The endoscope system 300 includes an endoscope 10, a control device 100, the image processing device 200, and a display 20.

The endoscope 10 is also referred to as a scope, which is inserted into a body of a patient to capture an image of an inside of the patient's body. At a distal end of the endoscope 10, an imaging device which images an inside of a body, and an illumination lens which irradiates an inside of a body with illumination light guided by a light guide from a light source are provided. In addition, at the distal end of the endoscope 10, a forceps port for inserting a treatment tool into a body may be provided. The endoscope 10 may be a flexible scope used for a digestive tract and the like, or a rigid scope used for surgical operation and the like.

The control device 100 performs image processing of an image signal transmitted from the imaging device of the endoscope 10, thereby generating an endoscopic image. In addition, the control device 100 controls each section of the endoscope system 300. The control device 100 is also referred to as a processor unit, a control box, etc. Note that the above endoscopic image generated by the control device 100 shall be referred to as a surgery image. That is, the surgery image is an image being captured in real time by an endoscope during surgery using the endoscope.

The display 20 displays the surgery image generated by the control device 100. In addition, the display 20 displays a bleeding stopping recommended point identified by the image processing device 200, thereby presenting the bleeding stopping recommended point to a surgeon as described later. The display 20 is also referred to as a display device or a monitor.

The image processing device 200 includes an acquisition section 220 and a processing section 210. In the first example configuration, the image processing device 200 is an information processing device such as a PC or a server provided separately from the control device 100.

The acquisition section 220 acquires the surgery image from the control device 100 and an internal body model from a diagnostic imaging device 500, and outputs them to the processing section 210. While various hardware can be assumed for the acquisition section 220, one example is such as a communication interface of an information processing device which is the image processing device 200, or a data interface of a processor configuring the processing section 210.

The diagnostic imaging device 500 is a device which captures an image of an inside of a patient's body and generates an internal body model of the patient based on data thereof. The internal body model may be generated before surgery using the endoscope, or may be generated in parallel with endoscopic imaging during the surgery. The diagnostic imaging device 500 is, for example, CT (Computed Tomography), MRI (magnetic resonance imaging), or an ultrasound scan device which are capable of capturing a 3D image of an inside of a body.

The processing section 210 identifies, based on the surgery image and the internal body model, a bleeding stopping recommended point in the surgery image, and causes the bleeding stopping recommended point to be superimposed on the surgery image and displayed on the display 20. The processing section 210 includes a blood vessel recognition section 211, an image comparison section 212, and a recommended point determination section 213.

The blood vessel recognition section 211 recognizes blood vessel running information from the internal body model. The blood vessel running information is information indicating how a blood vessel runs in a body of a patient, including information about a position of the blood vessel, bifurcation of the blood vessel, and a direction of blood flow. In addition, the blood vessel running information may include information about a size of the blood vessel or a depth of the blood vessel from an organ surface. In a case that the internal body model includes information about each tissue labeled in advance, the blood vessel recognition section 211 acquires, from such information, the blood vessel running information. Alternatively, the blood vessel recognition section 211 may extract the blood vessel running information from the internal body model using a recognition technique such as image recognition.

The image comparison section 212 compares the surgery image with the blood vessel running information, thereby matching a positional relationship between the surgery image and the blood vessel running information. For example, the image comparison section 212 matches a blood vessel captured in the surgery image with a blood vessel in the blood vessel running information using bifurcation of a major blood vessel and the like, thereby identifying which area in the blood vessel running information corresponds to a subject area captured in the surgery image. Alternatively, the blood vessel running information may include information about an organ or a tissue other than a blood vessel, and the image comparison section 212 may match an organ or a tissue captured in the surgery image with an organ or a tissue in the blood vessel running information.

The recommended point determination section 213 identifies the bleeding stopping recommended point based on the surgery image, the blood vessel running information, and correspondence between the surgery image and the blood vessel running information identified by the image comparison section 212. Specifically, the recommended point determination section 213 recognizes a bleeding position from the surgery image, identifies a bleeding position in the blood vessel running information corresponding to that bleeding position, and identifies the bleeding stopping recommended point on the surgery image corresponding to the bleeding position. Note that the bleeding position recognized from the surgery image is to be a first bleeding position. In addition, according to the correspondence between the surgery image and the blood vessel running information, the bleeding position in the blood vessel running information corresponding to the first bleeding position is to be a second bleeding position. The recommended point determination section 213 superimposes the bleeding stopping recommended point on the surgery image and displays the image on the display 20.

Figure 3:
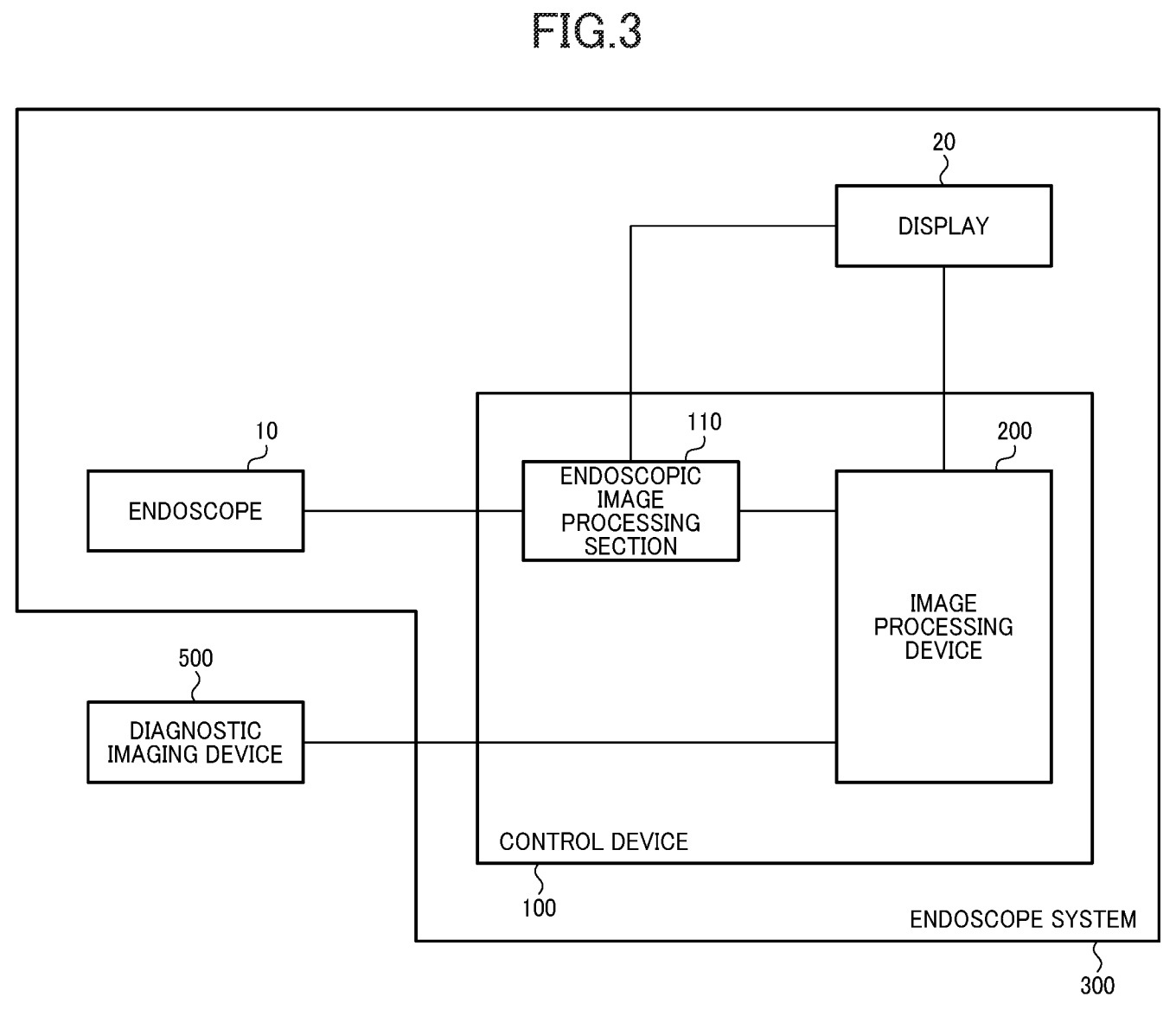

Note that the control device 100 of the endoscope system may be configured to include the image processing device 200. FIG. 3 shows a second example configuration of the endoscope system 300 in such case. The endoscope system 300 includes the endoscope 10, the control device 100, and the display 20. Note that description of components already described will be omitted as appropriate.

The control device 100 includes an endoscopic image processing section 110 and the image processing device 200. The endoscopic image processing section 110 performs image processing of an image signal transmitted from the imaging device of the endoscope 10, thereby generating a surgery image, and outputs the surgery image to the image processing device 200. For example, the endoscopic image processing section 110 performs processing such as development, tone correction, white balance, or noise reduction on the image signal, thereby generating the surgery image. The acquisition section 220 in the present example configuration is a data interface of a processor configuring the processing section 210. Alternatively, when a communication interface is provided on a circuit board on which the image processing device 200 is mounted, the acquisition section 220 may be the communication interface.

When performing a treatment of stopping bleeding occurred during surgery, it is preferable that a surgeon can properly recognize a bleeding stopping point. The aforementioned Japanese Unexamined Patent Application Publication No. 2011-36371 discloses a technique that estimates a bleeding start position from an image and notifies the bleeding start position to a surgeon. However, the Japanese Unexamined Patent Application Publication No. 2011-36371 does not disclose nor suggest identifying a bleeding stopping recommended point corresponding to the bleeding position or presenting the bleeding stopping recommended point to a surgeon.

In the above present embodiment, the image processing device 200 includes the acquisition section 220 which acquires a surgery image captured by the endoscope 10, and the processing section 210. The processing section 210 recognizes the first bleeding position from the surgery image, identifies a bleeding stopping recommended point being a recommended position of the bleeding stopping treatment corresponding to the first bleeding position, and performs processing in which the bleeding stopping recommended point is superimposed on the surgery image and displayed on the display 20.

As a result, in some embodiments, it is possible to present a bleeding stopping recommended point corresponding to a bleeding position to a surgeon, and the surgeon can immediately decide where to perform hemostasis by looking at the bleeding stopping recommended point thus presented. This enables the surgeon to perform the bleeding stopping treatment on a proper bleeding stopping point.

Note that the first bleeding position refers to a bleeding position in a surgery image, specifically, a position where bleeding from that position is recognized in the surgery image. The first bleeding position is also referred to as a first bleeding point. The bleeding stopping recommended point refers to a position recommended for performing the bleeding stopping treatment to stop bleeding in the first bleeding position. Note that the "point" of the "bleeding stopping recommended point" and the like may not be a single point. For example, the "point" may be such as an area of a certain size or a set of multiple points.

Further in the present embodiment, the processing section 210 recognizes the blood vessel running information indicating blood vessel running in a subject of the endoscope 10. Then, the processing section 210 identifies the second bleeding position in the blood vessel running information corresponding to the first bleeding position in the surgery image, and identifies a bleeding stopping point corresponding to the second bleeding position as the bleeding stopping recommended point.

As a result, in some embodiments, the first bleeding position in the surgery image is associated with the second bleeding position in the blood vessel running, and the bleeding stopping recommended point identified based on the second bleeding position in the blood vessel running is presented to a surgeon. This makes it possible to present the bleeding stopping recommended point in consideration of the blood vessel running to the surgeon. For example, as illustrated in the right figure of FIG. 1, it is preferable to stop bleeding upstream of a bleeding position and downstream of a bifurcation; by considering the blood vessel running, it is possible to present the preferable bleeding stopping recommended point to the surgeon.

Note that the second bleeding position refers to a bleeding position in the blood vessel running information. Specifically, the second bleeding position is a position in the blood vessel running information associated with the first bleeding position in the surgery image based on the positional relationship between the surgery image and the blood vessel running information matched by the image comparison section 212. The second bleeding position is also referred to as a second bleeding point.

Further in the present embodiment, the blood vessel running information is two-dimensional or three-dimensional information about a blood vessel of an inside of an organ, an image of which is captured by a method different from a method of capturing the surgery image.

As a result, in some embodiments, the blood vessel running information can be acquired by a method different from a method of capturing the surgery image, so that even the blood vessel running, which cannot be recognized or is difficult to recognize from the surgery image, can be recognized using the blood vessel running information. This makes it possible to present the bleeding stopping recommended point for a pool of blood or a blood vessel which is not on an organ surface to a surgeon, and the surgeon can properly perform the bleeding stopping treatment by referring to the bleeding stopping recommended point.

Although FIG. 2 illustrates an example in which the blood vessel running information is recognized from the internal body model captured in advance by the diagnostic imaging device 500, the method of recognizing the blood vessel running information is not limited thereto. For example, the blood vessel running information may be recognized from an image captured by the endoscope separately from the surgery image. In this case, the surgery image is a white light image, for example, and the blood vessel running information may be recognized from a special light image captured using special light different from white light. The special light image may be captured in advance or captured in real time in parallel with the surgery image by frame sequential illumination and the like. For example, illumination light of RDI (Red Dichromatic Imaging), illumination light of NBI (Narrow Band Imaging), or both can be assumed as the special light. RDI is an imaging method which increases the contrast between deep tissues by irradiating an inside of a body with green, amber, and red light. This method can capture an image of not only a blood vessel on an organ surface, but also a relatively deep blood vessel from the organ surface. NBI is a method of capturing an enhanced image of a blood vessel on a mucosal surface layer by irradiating an inside of a body with narrow band violet and green light.

A part or all of the image processing device 200 of the present embodiment as described above may be implemented by a program. Specifically, the program causes a computer to execute: recognizing the first bleeding position from a surgery image captured by an endoscope; identifying a bleeding stopping recommended point being a recommended position of the bleeding stopping treatment corresponding to the first bleeding position; and performing processing in which the bleeding stopping recommended point is superimposed on the surgery image and displayed on a display.

In this case, the image processing device 200 includes a memory which stores information, and a processor which operates based on the information stored in the memory. The information is, for example, such as a program and various data. The program describes some or all of the functions of the processing section 210 and the acquisition section 220. The processor executes the program, thereby implementing some or all of the functions of the processing section 210 and the acquisition section 220.

The processor includes hardware, which can include at least one of a circuit that processes digital signals and a circuit that processes analog signals. For example, the processor can be configured with one or more circuit devices or one or more circuit elements mounted on a circuit board. The one or more circuit devices are, for example, an IC and the like. The one or more circuit elements are, for example, a resistor, a capacitor, and the like. For example, the processor may be a CPU (Central Processing Unit). However, the processor is not limited to a CPU, and various processors such as a GPU (Graphics Processing Unit) or a DSP (Digital Signal Processor) can be used. In addition, the processor may include an integrated circuit device such as an ASIC (Application Specific Integrated Circuit) or a FPGA (Field Programmable Gate Array). Further, the processor may include an amplifier circuit, a filter circuit, and the like, which processes analog signals. The memory may be a semiconductor memory such as SRAM and DRAM, or a register, or a magnetic storage device such as a hard disk device, or an optical storage device such as an optical disk device. For example, the memory stores computer-readable instructions, which are executed by the processor to cause the functions of each section of the image processing device 200 to be implemented as processing. The instructions as referred to herein may be a set of instructions configuring the program, or the instructions instructing the hardware circuit of the processor to operate.

Furthermore, the above program can be stored in a non-transitory information storage medium, which is a computer-readable medium, for example. The information storage medium can be implemented by, for example, an optical disk, a memory card, an HDD, a semiconductor memory, or the like. The semiconductor memory is, for example, an ROM or a non-volatile memory. A part or all of the image processing device 200 performs various processes of the present embodiment based on the program and data stored in the information storage medium.

2. Third Example Configuration

Figure 4:
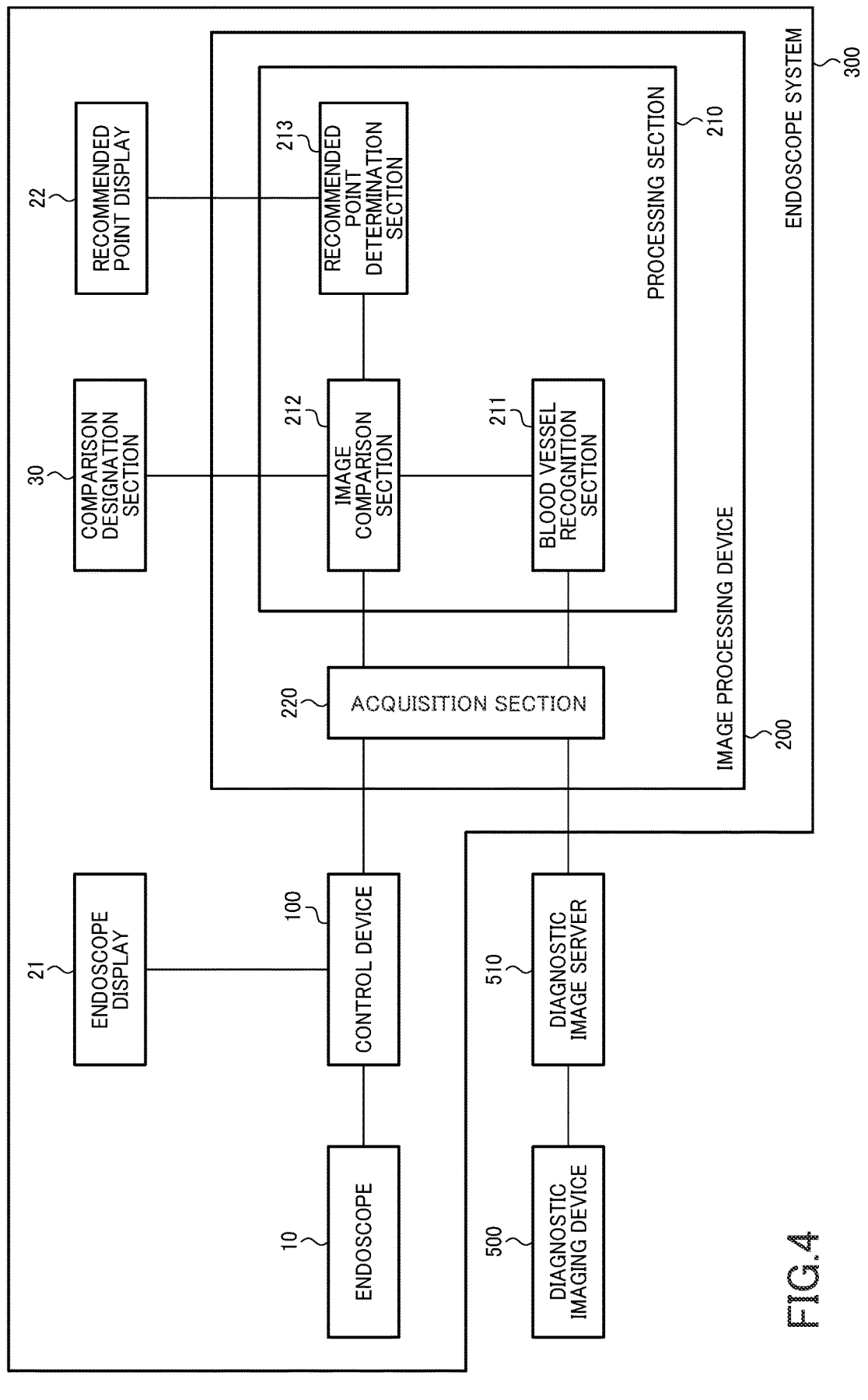
FIG. 4 is a third example configuration of the image processing device and the endoscope system.

FIG. 4 is a third example configuration of the image processing device 200 and the endoscope system 300. In the third example configuration, the endoscope system 300 includes two displays, i.e. an endoscope display 21 and a recommended point display 22. In addition, the endoscope system 300 includes a comparison designation section 30. Further, the acquisition section 220 acquires 3D data of the internal body model from a diagnostic image server 510. Note that description of components already described will be omitted as appropriate.

The endoscope display 21 displays an endoscopic image after image processing output by the control device 100. That is, the endoscope display 21 displays a surgery image on which no guide such as the bleeding stopping recommended point is superimposed. The recommended point display 22 displays the bleeding stopping recommended point output by the recommended point determination section 213. That is, the recommended point display 22 displays a surgery image on which the bleeding stopping recommended point is superimposed. Note that although illustrated herein is an example in which two displays are provided, one display may be provided where a surgery image with no guide such as the bleeding stopping recommended point superimposed may be displayed on a first display area thereof, and a surgery image with the bleeding stopping recommended point superimposed may be displayed on a second display area different from the first display area.

The diagnostic image server 510 stores image data for simulation. The image data for simulation is image data for diagnosis captured by the diagnostic imaging device 500, 3D volume data generated based on such data by pre-simulation upon planning surgery, or both. The acquisition section 220 acquires the image data for simulation stored in the diagnostic image server 510 as internal body data.

The comparison designation section 30 is an operation section for a surgeon to designate a comparison position of the surgery image and the blood vessel running information, designate whether or not to employ a comparison result output by the image comparison section 212, or both. The comparison designation section 30 is implemented by, for example, a pointing device, a switch, a button, a touch panel or the like.

When the comparison position of the surgery image and the blood vessel running information is input by the comparison designation section 30, the image comparison section 212 compares the surgery image with the blood vessel running information in the vicinity of the comparison position, thereby associating the positional relationship between the surgery image and the blood vessel running information. In addition, when an instruction for employing the comparison result is input from the comparison designation section 30, the image comparison section 212 outputs an association result of the surgery image with the blood vessel running information to the recommended point determination section 213, and when an instruction for not employing the comparison result is input from the comparison designation section 30, the image comparison section 212 does not output the association result of the surgery image with the blood vessel running information to the recommended point determination section 213. In the latter case, for example, a surgeon may input the association between the surgery image and the blood vessel running information from the comparison designation section 30, or the image comparison section 212 may perform the comparison again.

The image comparison section 212 performs matching processing of the blood vessel running information which is 3D data with the surgery image which is 2D data as follows, for example. That is, an arrangement relationship between an endoscope and an organ is mostly fixed according to the content of surgery, or the arrangement relationship between the endoscope and the organ can also be specified by pre-simulation and the like. Based on these information, it is possible to roughly estimate a position and a sight direction of a virtual endoscope camera in 3D internal body data. In addition, the detailed virtual camera position and the sight direction can be determined by comparing an organ, a blood vessel, a tissue or the like in the 3D internal body data viewed from the virtual endoscope camera with an organ, a blood vessel, a tissue or the like captured in an actual surgery image, and searching for the virtual camera position and the sight direction which enables matching therebetween. In this case, the blood vessel running that enters the field of view of the virtual endoscope camera in the 3D internal body data is associated with the blood vessel running captured in the actual surgery image. Note that the above is one example of matching processing, and a method of matching the surgery image with the blood vessel running information is not limited thereto. Various known methods can be employed, for example. For instance, the blood vessel running information may be 2D information as described above, and in such case, matching processing between two-dimensional images may be used.

Figure 5:
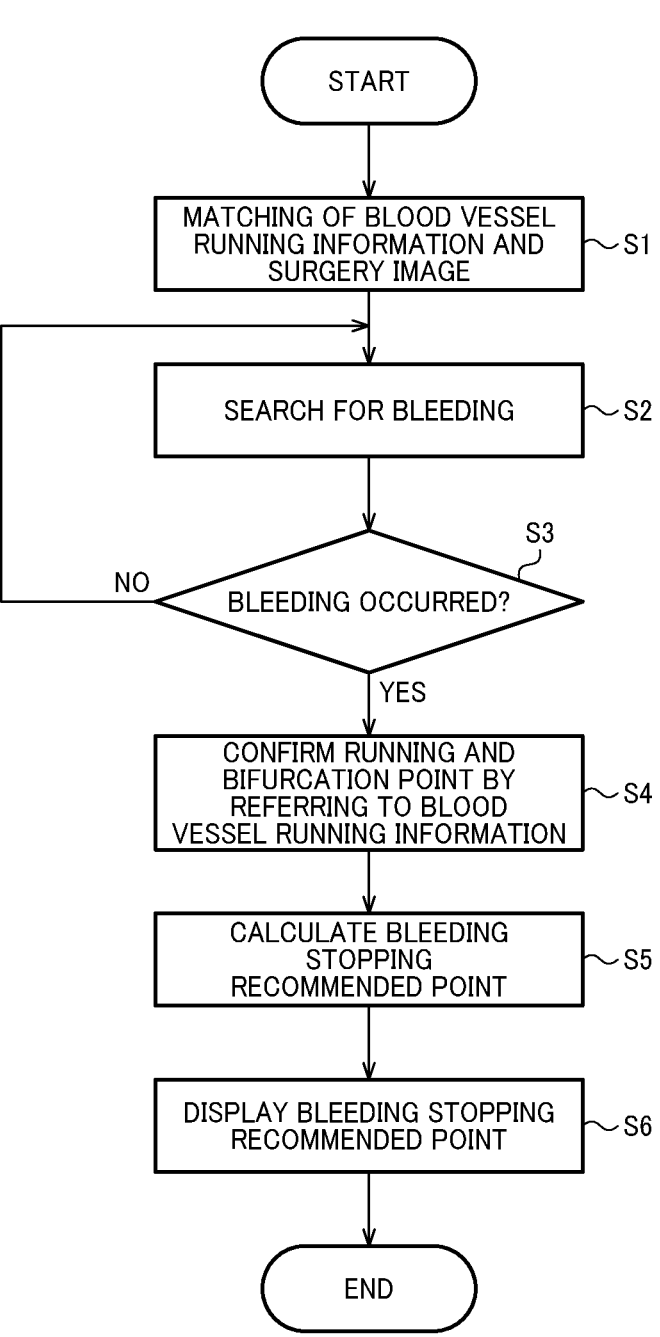
FIG. 5 is a flowchart of processing performed by the image processing device.
Figure 6:
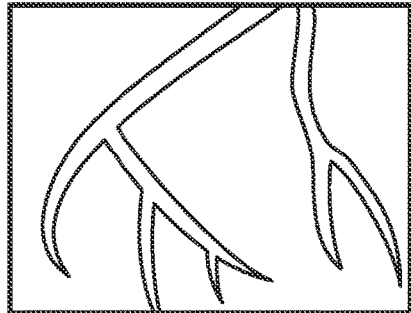
FIG. 6 is a diagram illustrating processing performed by the image processing device.
Figure 6:
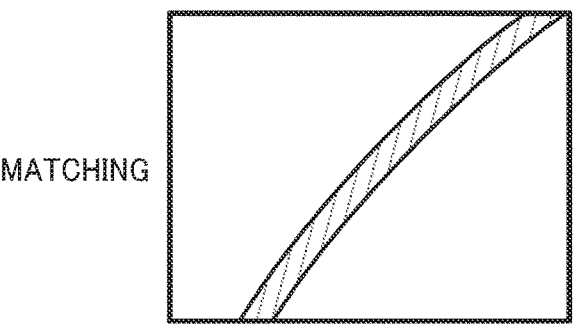
Figure 6:
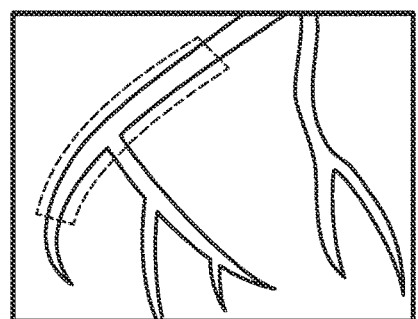
Figure 6:
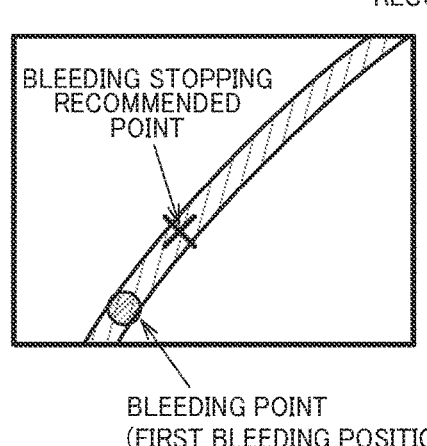
Figure 6:
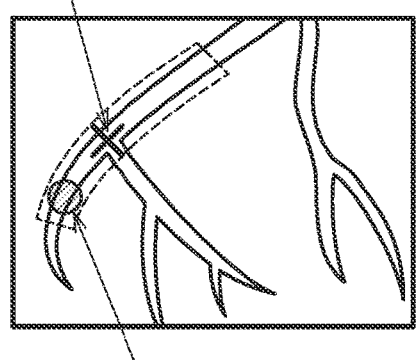

FIG. 5 is a flowchart of processing performed by the image processing device 200. FIG. 6 is a diagram illustrating processing performed by the image processing device 200.

As shown in the step S1 and the upper row of FIG. 6, the blood vessel recognition section 211 recognizes the blood vessel running information based on the internal body data acquired by the acquisition section 220 from the diagnostic image server 510. As shown in the middle row of FIG. 6, the image comparison section 212 matches the positional relationship between the surgery image and the blood vessel running information. The middle row of FIG. 6 shows that a blood vessel area hatched in the left endoscopic image is associated with a blood vessel area surrounded by a dotted line in the right blood vessel running information.

Note that the blood vessel recognition section 211 may recognize the blood vessel running information from the image data for diagnosis captured by the diagnostic imaging device 500, or may recognize the blood vessel running information from the 3D volume data generated by pre-simulation. In addition, the image comparison section 212 may extract a blood vessel on an organ surface from a special light image, and perform more accurate matching using the information thereof.

In the step S2, the recommended point determination section 213 recognizes a bleeding point from the surgery image. The recommended point determination section 213 detects the bleeding point from the surgery image by image recognition based on features of the image, or may detect the bleeding point from the surgery image using a trained model which is trained through machine learning to recognize the bleeding point from the surgery image.

In the step S3, the recommended point determination section 213 determines whether or not the bleeding point is detected in the step S2. When the bleeding point is not detected in the step S2, return to the step S2. When the bleeding point is detected in the step S2, as shown in the lower row of FIG. 6, proceed to the step S4. This bleeding point detected in the step S2 is to be the first bleeding position.

In the step S4, as shown in the lower row of FIG. 6, the recommended point determination section 213 identifies the second bleeding position in the blood vessel running information corresponding to the first bleeding position. The recommended point determination section 213 confirms running and bifurcation of the blood vessel by referring to the blood vessel running information.

In the step S5, the recommended point determination section 213 determines the bleeding stopping recommended point corresponding to the second bleeding position based on the running and bifurcation of the blood vessel confirmed in the step S4. In the step S6, the recommended point determination section 213 superimposes the bleeding stopping recommended point on the surgery image and displays on the recommended point display 22. The method of determining the bleeding stopping recommended point includes, for example, a first method of rule-based determination of the bleeding stopping recommended point using AI and the like, a second method of determining the bleeding stopping recommended point using a pre-simulation result, and a third method of determining the bleeding stopping recommended point by an algorithm without using AI or pre-simulation.

First, the first method will be described. Before surgery, a trained model is generated, which is trained by referring to past information. The past information includes a distance between a bleeding point and a bleeding stopping point, and a result of success/failure of bleeding stopping when the bleeding stopping was performed at the distance. During the surgery, an actual bleeding point during the surgery is input to the trained model and the trained model outputs the bleeding stopping recommended point, which is presented to a surgeon. This makes it possible to present the proper bleeding stopping recommended point based on the past success/failure of the bleeding stopping. In addition, even when pre-simulation is not performed, it is possible to present the bleeding stopping recommended point.

Figure 7:
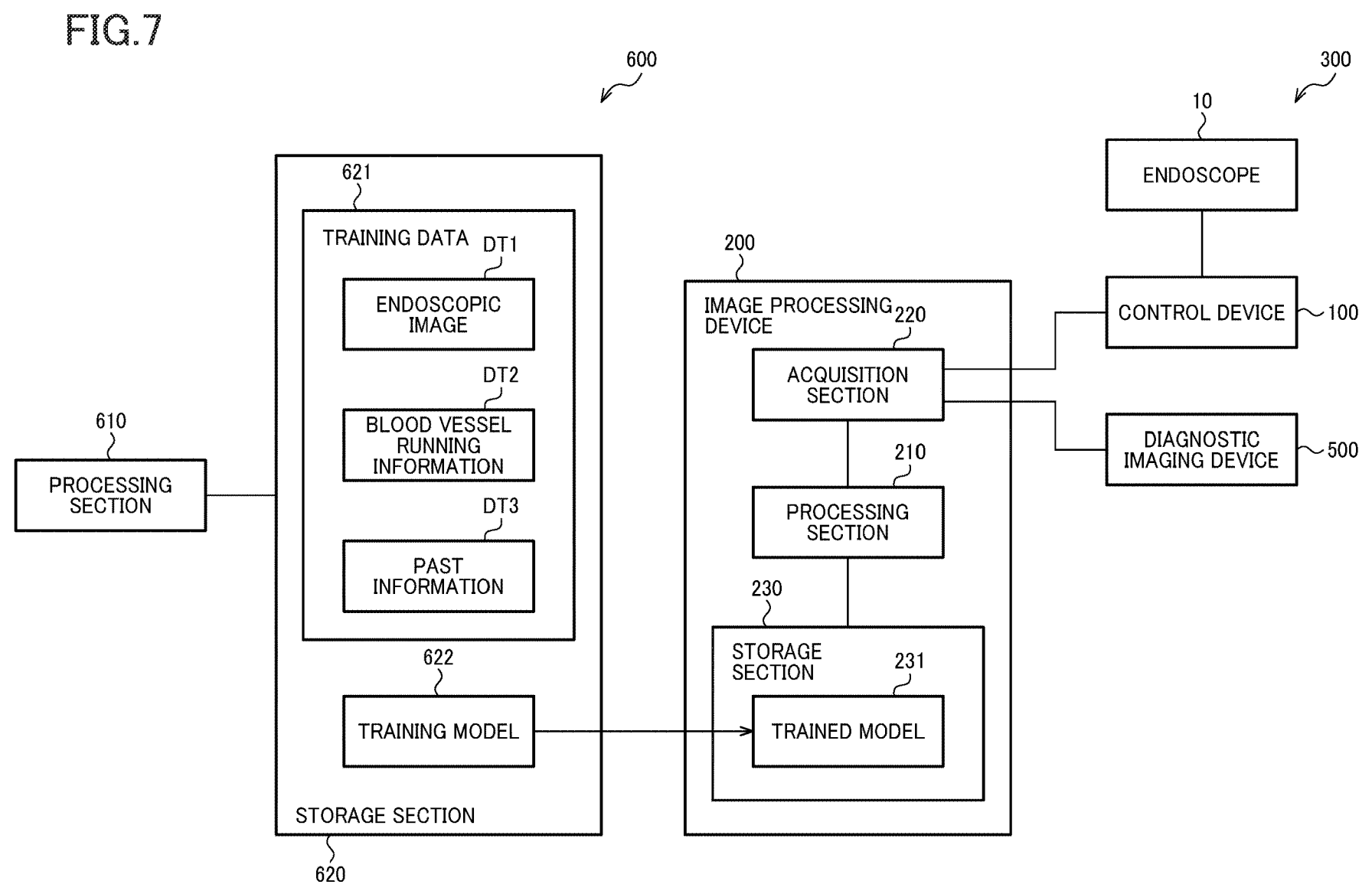

FIG. 7 is an example configuration of a training device 600 which generates a trained model, and the endoscope system 300 which presents the bleeding stopping recommended point using the trained model.

The training device 600 includes a processing section 610 and a storage section 620, and is configured with an information processing device such as a PC, for example. The processing section 610 is a processor such as a CPU. The storage section 620 is a memory device such as a semiconductor memory or a hard disk drive.

The storage section 620 stores training data 621 and a training model 622.

The training data includes an endoscopic image DT1, blood vessel running information DT2, and past information DT3. The past information DT3 is information regarding the bleeding stopping treatment performed in the past, including a bleeding point and a bleeding stopping point where the bleeding stopping treatment was actually performed on the bleeding point. In addition, as described above, the past information DT3 may include the distance between the bleeding point and the bleeding stopping point, and the result of success/failure of bleeding stopping when the bleeding stopping was performed at the distance.

The training model 622 receives the endoscopic image and the blood vessel running information as input data, recognizes the bleeding point and determines the bleeding stopping recommended point based on the input data, and outputs the bleeding point and the bleeding stopping recommended point as output data. The training model 622 is described by an algorithm using machine learning, and it is, for example, a neural network such as a CNN.

The processing section 610 inputs the endoscopic image DT1 and the blood vessel running information DT2 to the training model 622, thereby causing the training model 622 to infer the bleeding point and the bleeding stopping recommended point. The processing section 610 evaluates an error between the bleeding point and the bleeding stopping recommended point thus obtained and the past information DT3, and provides feedback to the training model 622 based on the error, thereby performing training processing on the training model 622. In this example, the past information DT3 corresponds to ground truth data. A feedback technique includes, for example, backpropagation.

The training model 622 after training is stored in a storage section 230 of the image processing device 200 as a trained model 231. The processing section 210 inputs the endoscopic image and the blood vessel running information to the trained model 231, thereby causing the trained model 231 to infer the bleeding point and the bleeding stopping recommended point. The endoscopic image herein is an image captured by the endoscope 10 during surgery, and the blood vessel running information is information acquired before or during the surgery using the diagnostic imaging device 500. The processing section 210 causes the bleeding stopping recommended point acquired by the inference to be superimposed on the endoscopic image and displayed on the recommended point display 22.

In the above first method, the image processing device 200 includes the storage section 230 which stores the trained model 231. The trained model 231 is trained to identify the bleeding stopping recommended point in the surgery image using information about the past bleeding stopping result. The processing section 210 identifies the bleeding stopping recommended point in the surgery image by processing using the trained model 231.

As a result, in some embodiments, the bleeding stopping treatment performed in the past can be used as a rule to determine the bleeding stopping recommended point which will give a similar bleeding stopping result. That is, by performing machine learning so as to obtain a bleeding stopping point with a good record of the past bleeding stopping result, it is possible to present the bleeding stopping recommended point appropriate for bleeding occurred during surgery. In addition, by using machine learning, the bleeding stopping recommended point can be determined in real time during surgery even when pre-simulation of the bleeding stopping point is not performed.

Next, the second method will be described. Before surgery, an operator performs simulation of the surgery. The operator refers to a surgeon or a group of medical workers including a surgeon. In the simulation, the operator simulates, as the bleeding stopping recommended point for each blood vessel area, a point to perform hemostasis when bleeding occurs in the area. This simulation result is stored in the diagnostic image server 510 as the 3D volume data. During the surgery, the recommended point determination section 213 uses the simulation result included in the 3D volume data to determine the bleeding stopping recommended point corresponding to the bleeding point. This makes it possible to preset a rule for determining the bleeding stopping recommended point. That is, the bleeding stopping recommended point can be determined by a rule that is not a black box.

Figure 8:
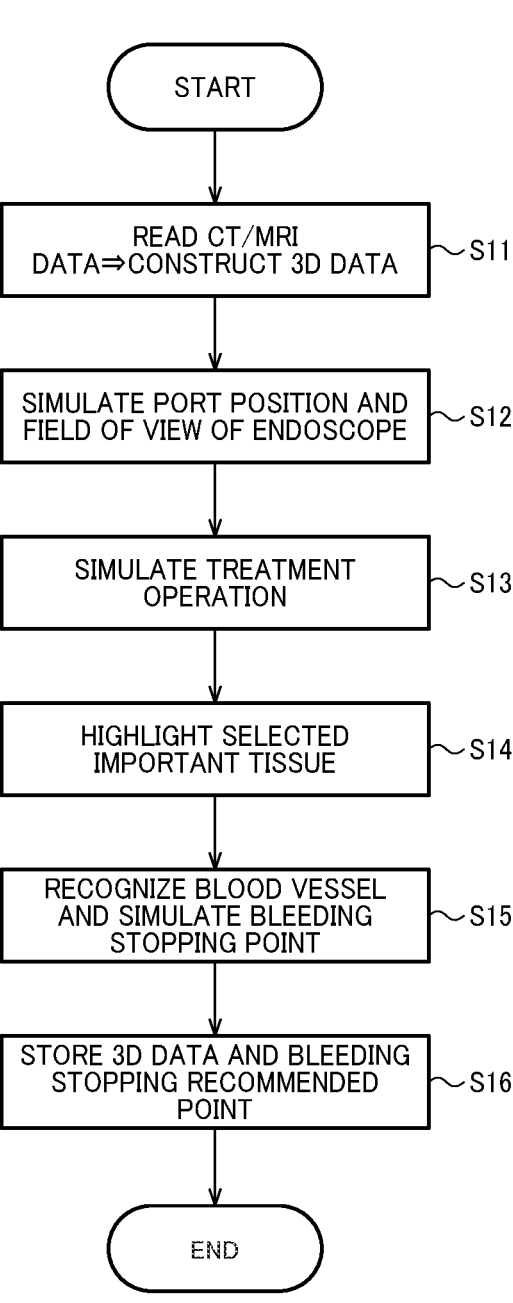
FIG. 8 is a flowchart illustrating a procedure of pre-simulation.
Figure 9:
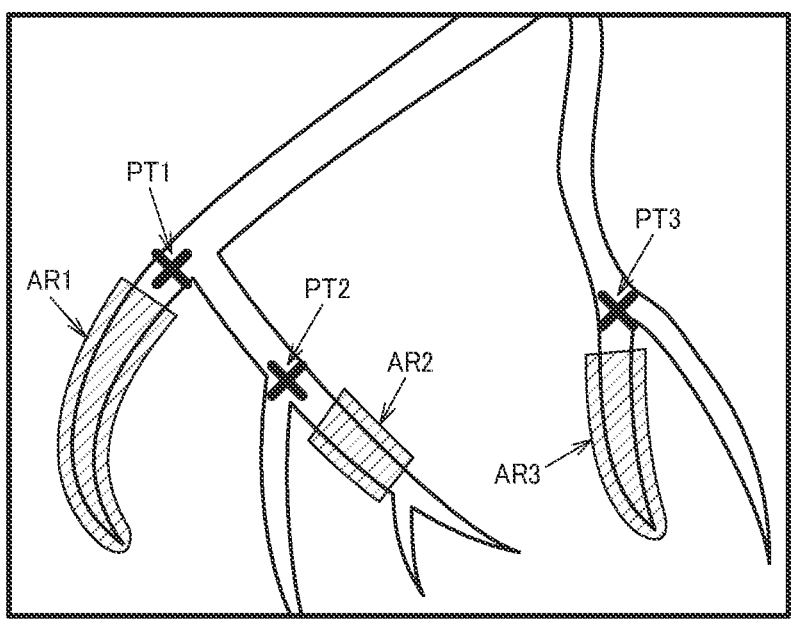
FIG. 9 is a diagram illustrating pre-simulation.

FIG. 8 is a flowchart illustrating a procedure of pre-simulation. FIG. 9 is a diagram illustrating the pre-simulation. Hereinafter, assumed is an example in which the pre-simulation is performed using a software for pre-simulation operating in an information processing device.

In the step S11, a simulation software reads CT data or MRI data and constructs, based on the data, 3D data of an inside of a patient's body. In the step S12, an operator simulates a position of a port to be provided on the patient and a field of view when inserting an endoscope into the port using the simulation software.

In the step S13, the operator simulates a treatment operation on an organ or a tissue to be operated using the simulation software. In the step S14, the operator selects an important tissue in the treatment operation and highlights the tissue displayed on the 3D data using the simulation software.

In the step S15, the operator recognizes a blood vessel in the 3D data, and simulates a bleeding stopping point in a case that bleeding occurs in the blood vessel. The operator inputs the bleeding stopping point determined by the simulation to the 3D data as the bleeding stopping recommended point. In the step S16, the simulation software stores the 3D data and the bleeding stopping recommended point input to the 3D data in the diagnostic image server 510.

As shown in FIG. 9, the operator designates a plurality of blood vessel areas AR1-AR3 in the 3D data and the bleeding stopping recommended points PT1-PT3 corresponding to the respective blood vessel areas. For example, the bleeding stopping recommended point PT1 is a bleeding stopping point recommended as a point where the bleeding stopping treatment will be performed if bleeding occurs in the blood vessel area AR1. Similarly, the blood vessel areas AR2 and AR3 are associated with the bleeding stopping recommended points PT2 and PT3. For example, the bleeding stopping recommended point is designated at the first bifurcation upstream of the blood vessel area, or at downstream thereof.

During surgery, for example, when the first bleeding position is determined as belonging to the blood vessel area AR1, the recommended point determination section 213 presents, as the bleeding stopping recommended point, the bleeding stopping recommended point PT1 associated with the blood vessel area AR1 to a surgeon.

In the above second method, the acquisition section 220 acquires information about the bleeding stopping recommended points PT1-PT3 corresponding to each of one or more blood vessel areas AR1-AR3 in the blood vessel running information. The processing section 210 identifies the blood vessel area among one or more blood vessel areas AR1-AR3, to which the second bleeding position belongs. The processing section 210 performs processing in which the bleeding stopping recommended point corresponding to the blood vessel area thus identified is superimposed on the surgery image and displayed on the display.

As a result, in some embodiments, in accordance with correspondence between the blood vessel area set in the pre-simulation and the bleeding stopping recommended point, it is possible to determine the bleeding stopping recommended point for a bleeding point occurred during surgery. This makes it possible to present the bleeding stopping recommended point to a surgeon in accordance with an explicit rule that is not a black box. In addition, it is possible to determine in advance in the pre-simulation a bleeding stopping point for each blood vessel area which is determined to be appropriate by the surgeon based on the 3D data of the inside of the patient's body and the like obtained by CT and the like.

Figure 10:
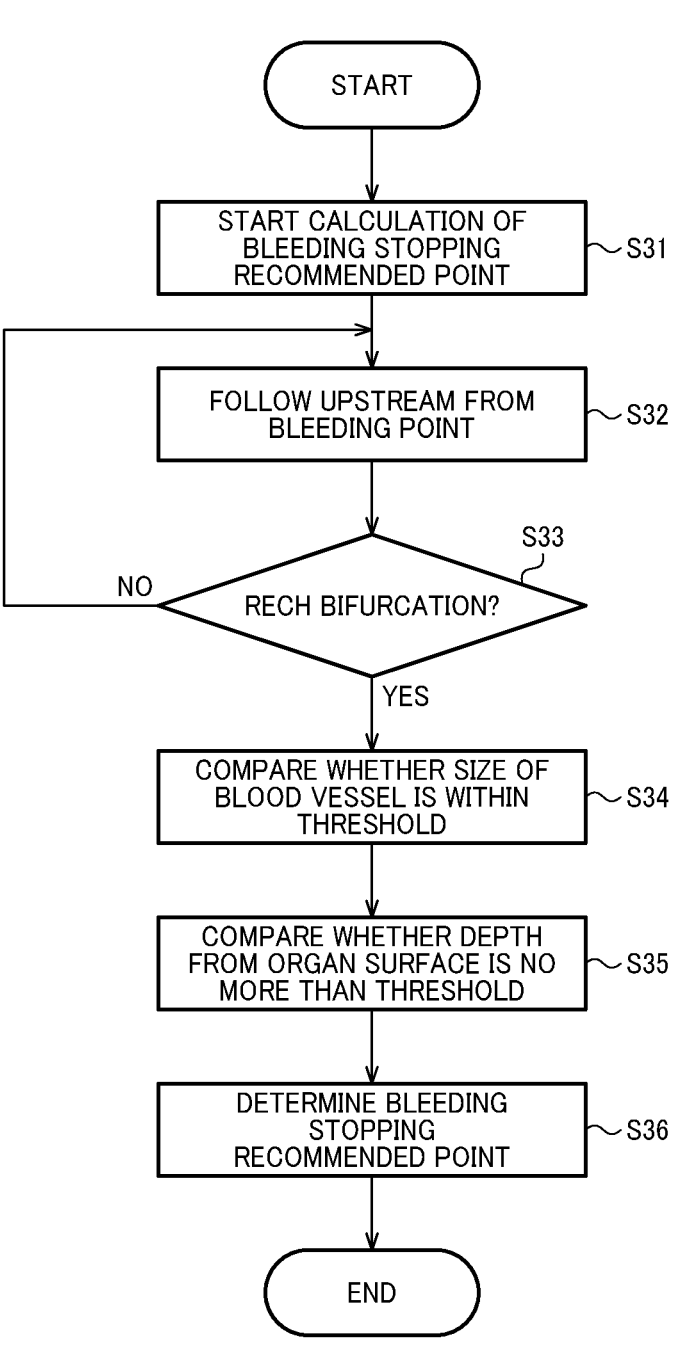
FIG. 10 is a flowchart of processing for determining a bleeding stopping recommended point in a third method.
Figure 11:
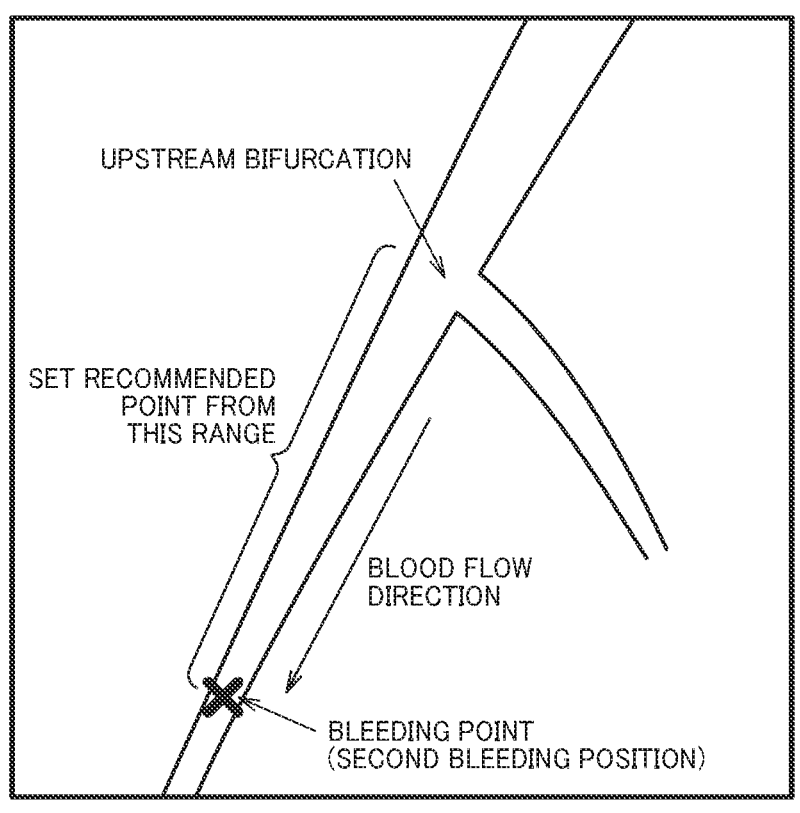
FIG. 11 is a diagram illustrating processing for determining a bleeding stopping recommended point in the third method.

Next, the third method will be described. FIG. 10 is a flowchart of processing for determining the bleeding stopping recommended point in the third method. FIG. 11 is a diagram illustrating the processing for determining the bleeding stopping recommended point in the third method.

In the step S31, when the first bleeding position is detected from the surgery image, the recommended point determination section 213 starts calculation of the bleeding stopping recommended point.

As shown in the step S32 and FIG. 11, the recommended point determination section 213 follows the blood vessel upstream from the second bleeding position in the blood vessel running information. In the step S33, the recommended point determination section 213 determines whether or not reaching a bifurcation of the blood vessel. The recommended point determination section 213 returns to the step S32 in a case of not reaching the bifurcation, and proceeds to the step S34 when reaching the bifurcation.

The recommended point determination section 213 searches for the bleeding stopping recommended point within the range from the second bleeding position to the upstream bifurcation. Specifically, in the step S34, the recommended point determination section 213 compares the size of the blood vessel with an acceptable threshold range of the size, and searches for a blood vessel position within the acceptable threshold range of the size. Further, in the step S35, the recommended point determination section 213 compares the depth of the blood vessel from the organ surface with a depth threshold, and searches for a blood vessel position with the depth of no more than the threshold. In the step S36, the recommended point determination section 213 determines a blood vessel position within the acceptable threshold range of the size and with the depth of no more than the threshold as the bleeding stopping recommended point.

Note that information about the size of the blood vessel can be extracted, for example, from 3D data captured by CT or MRI. Alternatively, an operator may attach the size information to the blood vessel in the 3D data in the pre-simulation. Information about the depth of the blood vessel can be extracted, for example, from 3D data captured by CT or MRI, or a special light image. In the special light image, the depth of the blood vessel can be estimated using the fact that the reaching depth in the tissue varies depending on a wavelength of illumination. Alternatively, the operator may attach the depth information to the blood vessel in the 3D data in the pre-simulation.

In the above third method, the processing section 210 searches for the bifurcation upstream of the second bleeding position in the blood vessel running information. In the blood vessel area between the second bleeding position and the upstream bifurcation, the processing section 210 identifies, as the bleeding stopping recommended point, a position where at least one of the size of the blood vessel or the depth of the blood vessel from the organ surface in the blood vessel running information is within a predetermined range.

As a result, in some embodiments, by searching for the bifurcation upstream of the second bleeding position after recognizing the bleeding point, it is possible to determine the bleeding stopping recommended point without using machine learning or pre-simulation. In addition, the bleeding stopping recommended point is determined based on at least one of the size of the blood vessel or the depth of the blood vessel from the organ surface, so that the blood vessel position with the size or the depth appropriate for the bleeding stopping treatment can be presented as the bleeding stopping recommended point. The bleeding stopping methods include cauterization, clipping, and the like, each of which has the appropriate size of the blood vessel. In addition, when stopping bleeding of a deep blood vessel from an organ surface, it is required to incise the organ surface to expose the blood vessel, followed by hemostasis. Accordingly, if the blood vessel at the bleeding stopping point is too deep, the bleeding stopping treatment can take longer. By considering the depth of the blood vessel, it is possible to present the bleeding stopping recommended point at a position where the bleeding stopping treatment will take relatively a little time.

3. Fourth Example Configuration

Figure 12:
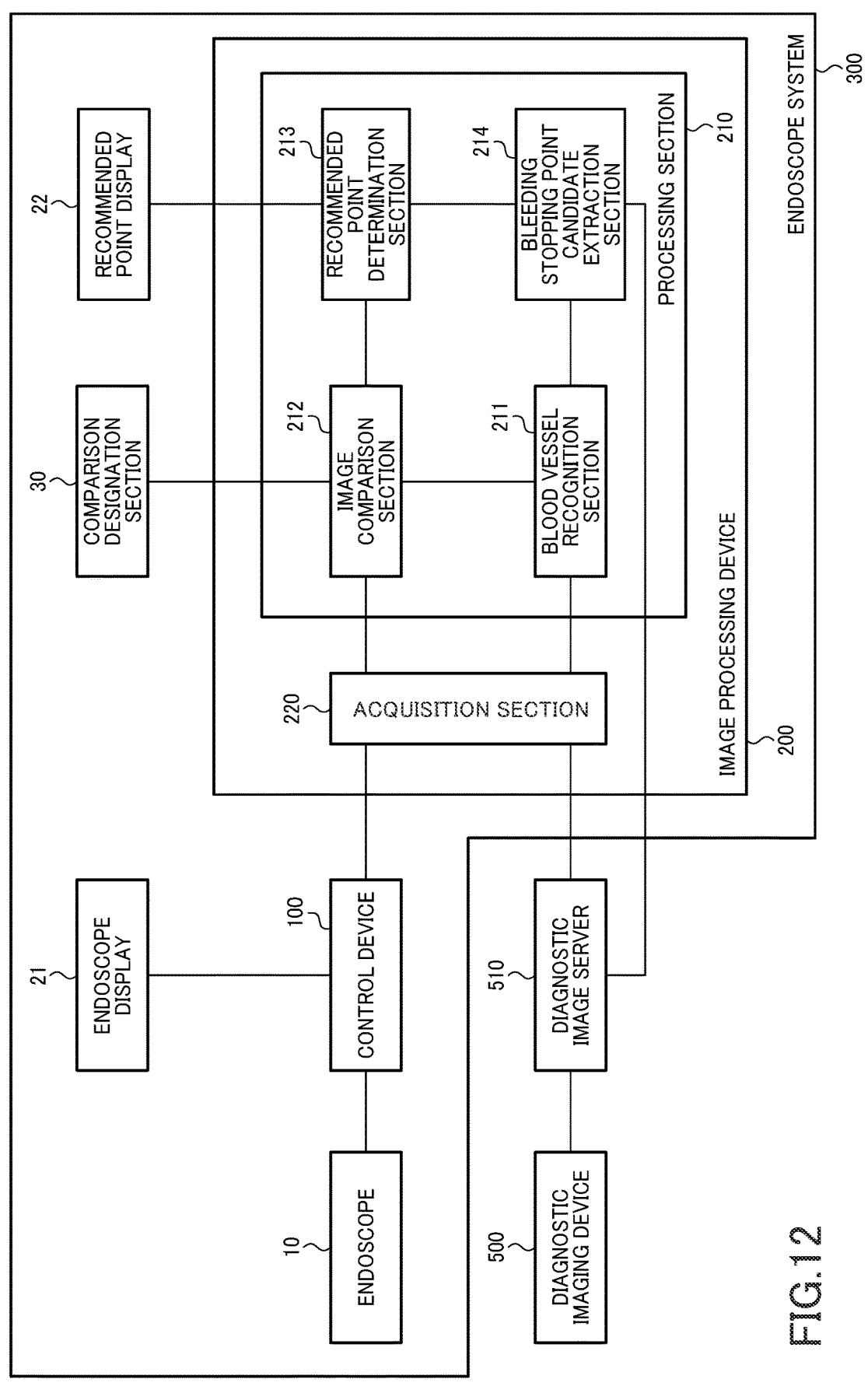
FIG. 12 is a fourth example configuration of the image processing device and the endoscope system.

FIG. 12 is a fourth example configuration of the image processing device 200 and the endoscope system 300. In the fourth example configuration, the processing section 210 further includes a bleeding stopping point candidate extraction section 214. Note that description of components already described will be omitted as appropriate.

The bleeding stopping point candidate extraction section 214 receives the image data for diagnosis, the image data for simulation, or both (i.e. internal body data). The bleeding stopping point candidate extraction section 214 recognizes a vascular bifurcation point in the blood vessel running based on the internal body data, and extracts a bleeding stopping point candidate for a blood vessel downstream of the bifurcation point. The extraction of the bleeding stopping point candidate is performed for each bifurcation and each blood vessel downstream of the bifurcation. That is, the bleeding stopping point candidate is associated with each downstream blood vessel, and there is a plurality of bleeding stopping point candidates.

The recommended point determination section 213 determines which blood vessel has a bleeding point in the blood vessel running information, selects the bleeding stopping point candidate associated with the blood vessel, and determines the bleeding stopping point candidate as the bleeding stopping recommended point. Accordingly, the bleeding stopping point candidate refers to a candidate point for the bleeding stopping point determined based on the blood vessel running and the bifurcation, a candidate point being selected as the bleeding stopping recommended point depending on the bleeding point.

Figure 13:
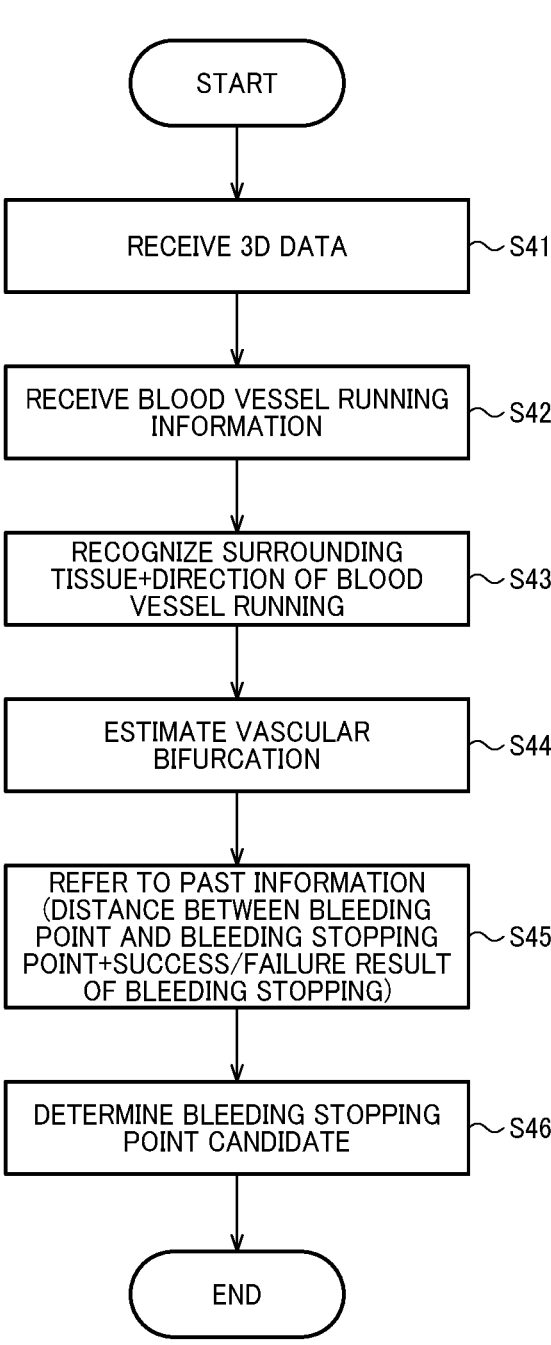
FIG. 13 is a flowchart of extraction of a bleeding stopping point candidate during surgery.
Figure 14:
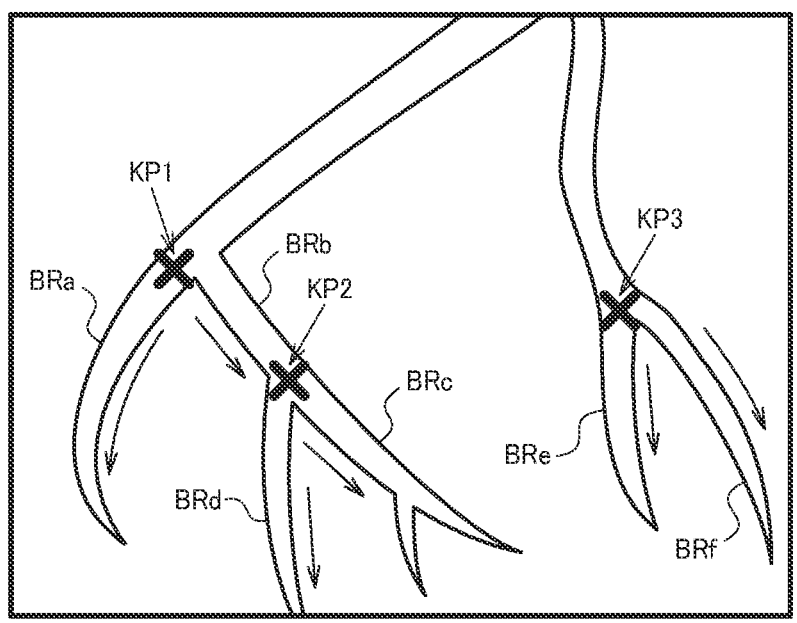
FIG. 14 is a diagram illustrating extraction of a bleeding stopping point candidate.

FIG. 13 is a flowchart of extraction of the bleeding stopping point candidate during surgery. FIG. 14 is a diagram illustrating the extraction of the bleeding stopping point candidate. In the step S41, the bleeding stopping point candidate extraction section 214 receives the image data for diagnosis, the image data for simulation, or both (i.e. internal body data). In the step S42, the bleeding stopping point candidate extraction section 214 receives the blood vessel running information recognized by the blood vessel recognition section 211.

As shown in the step S43 and FIG. 14, the bleeding stopping point candidate extraction section 214 recognizes tissue (anatomy) information and a direction of blood flow from the internal body data and the blood vessel running information. In FIG. 14, the arrows indicate the direction of the blood flow. In the step S44, the bleeding stopping point candidate extraction section 214 recognizes the bifurcation of the blood vessel based on the direction of the blood flow. In FIG. 14, branches of the blood vessel classified by the vascular bifurcation are indicated by Bra-BRf. The branch means a blood vessel area from the bifurcation to an end of the blood vessel or a blood vessel area between bifurcations. While an artery is exemplified in the specification, the same applies to a vein.

In the steps S45 and S46, the bleeding stopping point candidate extraction section 214 determines, based on the blood flow direction in each branch and the vascular bifurcation, the bleeding stopping point candidate where bleeding can properly be stopped when bleeding occurs in each branch. In the example of FIG. 14, the branch BRa is associated with the bleeding stopping point candidate KP1, the branches BRc and BRd are associated with the bleeding stopping point candidate KP2, and the branches BRe and BRf are associated with the bleeding stopping point candidate KP3. The bleeding stopping point candidate extraction section 214 determines the bleeding stopping point candidate by referring to the past information. The past information includes the distance between the bleeding point and the bleeding stopping point, as well as the result of success/failure of bleeding stopping when the bleeding stopping was performed at the distance. Specifically, the bleeding stopping point candidate extraction section 214 refers to a relationship between a similar bleeding point and a bleeding stopping point for each bifurcation in the past information, i.e. the position of the bleeding stopping point when the bleeding point was in the bifurcation, and determines, based on the information, the bleeding stopping point candidate on the basis of each bifurcation.

The bleeding stopping point candidate extraction section 214 extracts the bleeding stopping point candidate, for example, by processing using machine learning. In this case, a training model is trained in advance such that the bleeding stopping point candidate will be output when the internal body data, the blood vessel running information, and the past information are input. Then, during surgery, the bleeding stopping point candidate extraction section 214 determines the bleeding stopping point candidate based on the internal body data, the blood vessel running information, and the past information by inference processing using the trained model. Alternatively, a program may be created that incorporates an algorithm to determine the bleeding stopping point candidate in accordance with a rule for bifurcation determination and a rule for determining the bleeding stopping point candidate based on the bifurcation. In this case, a processor configuring the processing section 210 executes the above program, thereby implementing the processing of the bleeding stopping point candidate extraction section 214.

The recommended point determination section 213 receives the second bleeding position determined by the image comparison section 212. The recommended point determination section 213 determines to which branch of the blood vessel classified based on the bifurcation the second bleeding position belongs, and determines the bleeding stopping point candidate corresponding to the branch as the bleeding stopping recommended point. The recommended point determination section 213 may determine the bleeding stopping point candidate using the methods illustrated in FIGS. 10 and 11, in consideration of the size or the depth of the blood vessel. In addition, the recommended point determination section 213 may make a choice of the bleeding stopping point candidate according to the distance between the second bleeding position and the bleeding stopping point candidate. The description will be given below.

When the second bleeding position is too close to the bleeding stopping point candidate, for example, closer than a first predetermined distance, the recommended point determination section 213 selects, as the bleeding stopping recommended point, a bleeding stopping point candidate which is away from the second bleeding position by the first predetermined distance or more. In addition, when the second bleeding position is too far from the bleeding stopping point candidate, for example, far away by more than a second predetermined distance, the recommended point determination section 213 re-sets the bleeding stopping point candidate at a position closer than the second predetermined distance, and determines that bleeding stopping point candidate as the bleeding stopping recommended point. That is, even if there is no other bleeding stopping point candidate between the second bleeding position and the first bleeding stopping point candidate upstream thereof, a new bleeding stopping point candidate is set at a point closer than the second predetermined distance.

In the above embodiment, the processing section 210 extracts the bleeding stopping point candidates KP1-KP3 corresponding to each of one or more blood vessel areas in the blood vessel running information based on the direction of the blood flow and the vascular bifurcation in the blood vessel running information. Note that in the above, the branches Bra-BRf correspond to the blood vessel areas. The processing section 210 identifies the blood vessel area among the one or more blood vessel areas, to which the second bleeding position belongs, and identifies the bleeding stopping point candidate corresponding to the identified blood vessel area as the bleeding stopping recommended point.

As a result, in some embodiments, it is possible to select the bleeding stopping recommended point corresponding to the bleeding point from the bleeding stopping point candidates extracted in advance by the processing section 210 while considering the bifurcation and the like. By extracting the bleeding stopping point candidates in advance, it is possible to use extraction processing with a greater processing load than a case of obtaining the bleeding stopping recommended point in real time after recognizing the bleeding point, allowing highly accurate extraction of the bleeding stopping point candidates. Further, after recognizing the bleeding point, it is only necessary to select the bleeding stopping recommended point from the bleeding stopping point candidates, whereby reducing a processing load.

4. Highlighting of Blood Vessel to be Affected by Bleeding Stopping

Figure 15:
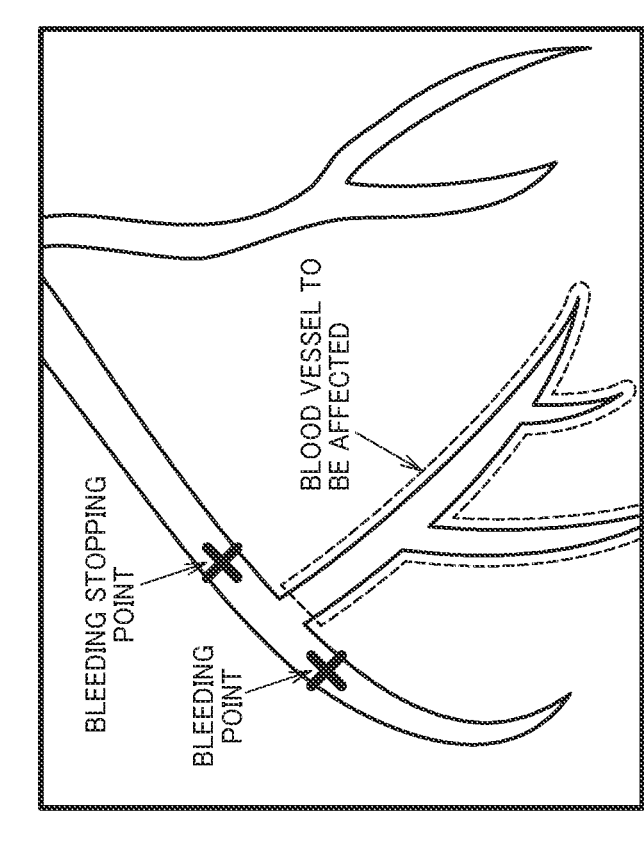
FIG. 15 is an example of highlighting of a blood vessel to be affected by bleeding stopping.
Figure 15:
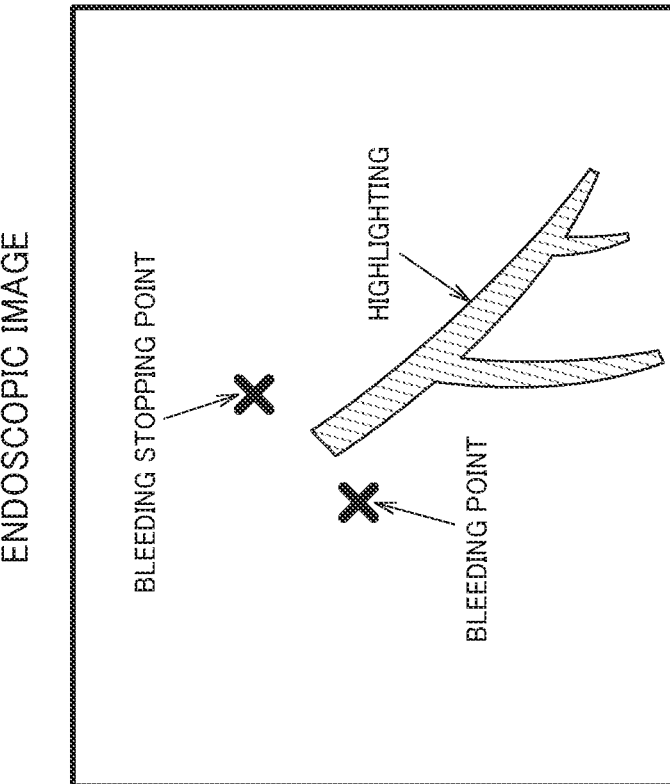

FIG. 15 shows an example of highlighting of a blood vessel to be affected by bleeding stopping. This highlighting is applicable to any of the first to fourth example configurations.

The recommended point determination section 213 displays, as "a blood vessel to be affected by bleeding stopping", a blood vessel downstream of the bleeding stopping recommended point superimposed on the endoscopic image. Specifically, as shown in the right figure of FIG. 15, suppose that the bleeding stopping recommended point is set upstream of the first bifurcation upstream of the bleeding point. In this case, there are branches having a possibility that the blood flow stops due to the bleeding stopping, in addition to a branch having the bleeding point. In FIG. 15, such blood vessel is surrounded by a dotted line. As shown in the left figure of FIG. 15, the recommended point determination section 213 highlights an area on the endoscopic image corresponding to the blood vessel having a possibility that the blood flow stops due to the bleeding stopping, using a highlight or the like. This highlighting is superimposed together with the display of the bleeding stopping recommended point on the endoscopic image.

In the above embodiment, the processing section 210 performs processing of highlighting an area in the surgery image that will be affected when the bleeding stopping treatment is performed on the bleeding stopping recommended point.

As a result, in some embodiments, a surgeon can determine whether or not to perform the bleeding stopping treatment on the bleeding stopping recommended point by looking at the highlighting in the surgery image. For example, if a blood vessel of a tissue to be removed by surgery is affected, bleeding stopping at that point is unlikely to cause problems. On the other hand, if a blood vessel of a tissue that will not be removed is affected, the surgeon can take action such as changing the bleeding stopping point.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

The invention claimed is:

1. An image processing device comprising:
a processor configured to:
   acquire a surgery image captured by an endoscope;
   recognize blood vessel running information indicating blood vessel running in a subject of the endoscope;
   recognize a first bleeding position from the surgery image;

identify a second bleeding position in the blood vessel running information corresponding to the first bleeding position in the surgery image;
   identify a bleeding stopping recommended point corresponding to the second bleeding position based on a direction of blood flow and a vascular bifurcation in the blood vessel running information; and
   perform processing in which the identified bleeding stopping recommended point is superimposed on the surgery image and displayed on a display.

2. The image processing device as defined in claim 1, wherein the blood vessel running information is two-dimensional or three-dimensional information about a blood vessel of an inside of an organ, an image of which is captured by a method different from a method of capturing the surgery image.

3. The image processing device as defined in claim 1, wherein a trained model is trained to identify the bleeding stopping recommended point in the surgery image using information about a past bleeding stopping result, wherein the processor is configured to identify the bleeding stopping recommended point in the surgery image by processing using the trained model.

4. The image processing device as defined in claim 1, wherein the processor is configured to:
   extract a bleeding stopping point candidate corresponding to each of one or more blood vessel areas in the blood vessel running information based on the direction of blood flow and the vascular bifurcation in the blood vessel running information;
   identify the blood vessel area among the one or more blood vessel areas, to which the second bleeding position belongs; and
   identify the bleeding stopping point candidate corresponding to the identified blood vessel area as the bleeding stopping recommended point.

5. The image processing device as defined in claim 1, wherein the processor is configured to:
   search for a bifurcation upstream of the second bleeding position in the blood vessel running information; and
   identify, in a blood vessel area between the second bleeding position and the bifurcation upstream thereof, a position in the blood vessel running information where at least one of a size of a blood vessel or a depth of the blood vessel from an organ surface is within a predetermined range as the bleeding stopping recommended point.

6. The image processing device as defined in claim 1, wherein the processor is further configured to perform processing of highlighting an area in the surgery image, the area being affected when bleeding stopping treatment is performed on the bleeding stopping recommended point.

7. An endoscope system, comprising:
the image processing device, the endoscope, and the display as defined in claim 1.

8. The image processing device as defined in claim 1, wherein the processor is configured to:
   acquire information about a bleeding stopping recommended point corresponding to each of one or more blood vessel areas in the blood vessel running information;
   identify the blood vessel area among the one or more blood vessel areas, to which the second bleeding position belongs; and perform processing in which the bleeding stopping recommended point corresponding to the identified blood vessel area is superimposed on the surgery image and displayed on the display.

9. The image processing device as defined in claim 8, wherein the processor is configured to:

extract a bleeding stopping point candidate corresponding to each of one or more blood vessel areas in the blood vessel running information based on the direction of blood flow and the vascular bifurcation in the blood vessel running information;

identify the blood vessel area among the one or more blood vessel areas, to which the second bleeding position belongs; and identify the bleeding stopping point candidate corresponding to the identified blood vessel area as the bleeding stopping recommended point.

10. An image processing method, comprising:

recognizing blood vessel running information indicating blood vessel running in a subject of an endoscope;

recognizing a first bleeding position from a surgery image captured by the endoscope;

identifying a second bleeding position in the blood vessel running information corresponding to the first bleeding position in the surgery image;

identifying a bleeding stopping recommended point corresponding to the second bleeding position based on a direction of blood flow and a vascular bifurcation in the blood vessel running information; and performing processing in which the identified bleeding stopping recommended point is superimposed on the surgery image and displayed on a display.

11. The image processing method as defined in claim 10, wherein the blood vessel running information is two-dimensional or three-dimensional information about a blood vessel of an inside of an organ, an image of which is captured by a method different from a method of capturing the surgery image.

12. The image processing method as defined in claim 10, comprising:

identifying the bleeding stopping recommended point in the surgery image by processing using a trained model trained to identify the bleeding stopping recommended point in the surgery image using information about a past bleeding stopping result.

13. The image processing method as defined in claim 10, comprising:

extracting a bleeding stopping point candidate corresponding to each of one or more blood vessel areas in the blood vessel running information based on the direction of blood flow and the vascular bifurcation in the blood vessel running information;

identifying the blood vessel area among the one or more blood vessel areas, to which the second bleeding position belongs; and identifying the bleeding stopping point candidate corresponding to the identified blood vessel area as the bleeding stopping recommended point.

14. The image processing method as defined in claim 10, comprising:

searching for a bifurcation upstream of the second bleeding position in the blood vessel running information; and identifying, in a blood vessel area between the second bleeding position and the bifurcation upstream thereof, a position in the blood vessel running information where at least one of a size of a blood vessel or a depth of the blood vessel from an organ surface is within a predetermined range as the bleeding stopping recommended point.

15. The image processing method as defined in claim 10, comprising:

performing processing of highlighting an area in the surgery image, the area being affected when bleeding stopping treatment is performed on the bleeding stopping recommended point.

16. The image processing method as defined in claim 10, comprising acquiring information about a bleeding stopping recommended point corresponding to each of one or more blood vessel areas in the blood vessel running information;

identifying the blood vessel area among the one or more blood vessel areas, to which the second bleeding position belongs; and performing processing in which the bleeding stopping recommended point corresponding to the identified blood vessel area is superimposed on the surgery image and displayed on the display.

17. The image processing method as defined in claim 16, comprising:

extracting a bleeding stopping point candidate corresponding to each of one or more blood vessel areas in the blood vessel running information based on the direction of blood flow and the vascular bifurcation in the blood vessel running information;

identifying the blood vessel area among the one or more blood vessel areas, to which the second bleeding position belongs; and identifying the bleeding stopping point candidate corresponding to the identified blood vessel area as the bleeding stopping recommended point.

18. A non-transitory information storage medium storing a program causing a computer to execute:

recognizing blood vessel running information indicating blood vessel running in a subject of an endoscope;

recognizing a first bleeding position from a surgery image captured by the endoscope;

identifying a second bleeding position in the blood vessel running information corresponding to the first bleeding position in the surgery image;

identifying a bleeding stopping recommended point corresponding to the second bleeding position based on a direction of blood flow and a vascular bifurcation in the blood vessel running information; and performing processing in which the identified bleeding stopping recommended point is superimposed on the surgery image and displayed on a display.

* * * * *